United States Patent
Kim et al.

(10) Patent No.: US 9,651,221 B2
(45) Date of Patent: May 16, 2017

(54) OPTICAL IMAGING SYSTEM WITH IMPROVED RESOLUTION

(71) Applicant: Industry-Academic Cooperation Foundation, Yonsei University, Seoul (KR)

(72) Inventors: Dong Hyun Kim, Seoul (KR); Won-ju Lee, Seoul (KR); Hongki Lee, Seoul (KR)

(73) Assignee: Industry-Academic Cooperation Foundation, Yonsei University, Seoul (KR)

( * ) Notice: Subject to any disclaimer, the term of this patent is extended or adjusted under 35 U.S.C. 154(b) by 101 days.

(21) Appl. No.: 14/454,166

(22) Filed: Aug. 7, 2014

(65) Prior Publication Data
US 2015/0041680 A1    Feb. 12, 2015

(30) Foreign Application Priority Data

Aug. 7, 2013 (KR) .................. 10-2013-0093767

(51) Int. Cl.
*G01N 21/64* (2006.01)
*F21V 9/16* (2006.01)

(52) U.S. Cl.
CPC ............. *F21V 9/16* (2013.01); *G01N 21/648* (2013.01); *G01N 21/6452* (2013.01); *G01N 2021/6419* (2013.01)

(58) Field of Classification Search
CPC ........................................................ F21V 9/16
See application file for complete search history.

(56) References Cited

U.S. PATENT DOCUMENTS

| 6,667,830 B1* | 12/2003 | Iketaki | ................. G01N 21/636 250/458.1 |
| 2013/0327928 A1* | 12/2013 | Leach | .................... B82Y 20/00 250/216 |

FOREIGN PATENT DOCUMENTS

| KR | 10-2004-0039553 | 5/2004 |
| KR | 10-2007-0080914 | 8/2007 |
| KR | 10-2010-0061603 | 6/2010 |
| KR | 10-2013-0017718 | 2/2013 |

OTHER PUBLICATIONS

Nikon Corporation, "MicroscopyU / Numerical Aperture" retrieved from Internet Feb. 10, 2016.*

* cited by examiner

*Primary Examiner* — Edwin Gunberg
(74) *Attorney, Agent, or Firm* — Mintz Levin Cohn Ferris Glovsky and Popeo, P.C.; Kongsik Kim; Jonathon Western

(57) ABSTRACT

Disclosed is an optical imaging system having improved resolution. The disclosed optical imaging system may include a substrate on which a specimen dyed with a fluorescent material is placed; a multiple number of dimer nanopillars formed on the substrate; and a light source unit configured to provide a light source to the substrate, where the light source unit provides an incident ray to the substrate from a first light source to excite the fluorescent material, and afterwards turns off the first light source and activates a second light source and a third light source simultaneously to provide incident rays to the substrate. The disclosed optical imaging system can provide a resolution that is higher than the diffraction limit.

5 Claims, 7 Drawing Sheets

- PRIOR ART -

- PRIOR ART -

OPTICAL IMAGING SYSTEM WITH IMPROVED RESOLUTION

CROSS-REFERENCE TO RELATED APPLICATIONS

This application claims the benefit of Korean Patent Application No. 10-2013-0093767, filed with the Korean Intellectual Property Office on Aug. 7, 2013, the disclosure of which is incorporated herein by reference in its entirety.

BACKGROUND

1. Technical Field

The present invention relates to an optical imaging system, more particularly to an optical imaging system that is capable of providing improved resolution.

2. Description of the Related Art

Biotechnology is fast rising as a next-generation industry, and accordingly, various bio-imaging techniques are being developed in the field of measurement systems.

A conventional TIR microscope may be structured to excite a fluorescent material that is dyed into a specimen, by using evanescent waves localized along the depth direction that are created when an incident beam undergoes total reflection at the interface between the specimen and a substrate, and to detect the fluorescence signals emitted from the excited fluorescent material and convert them into an image.

However, with the conventional TIR microscope, it is difficult or impossible to detect molecules or molecule trajectories, etc., in the horizontal direction which are smaller than the resolution limit that can be calculated by Abbe's equation of diffraction.

Thus, there is a need for a TIR microscope that not only provides a high resolution in the depth direction but also provides a high resolution in the horizontal direction.

FIG. 1 illustrates the structure of light incidence in an optical imaging system according to the related art.

Referring to FIG. 1, a conventional optical imaging system may include a substrate 100, a multiple number of dimer nanopillars 110, and a first light source 120.

A specimen dyed with a fluorescent material may be placed on the substrate 100, and the first light source 120 may apply an incident ray on the substrate. Here, the first light source may cause total reflection of the incident ray at the interface between the specimen and the substrate, thereby exciting the fluorescent material and causing the fluorescent material to emit light.

The multiple dimer nanopillars 110 formed on the substrate 100 may be structured such that two nanopillars are near each other. When using dimer nanopillars 110, an incident ray may generate a locally activated surface electric field (a hotspot), and as the fluorescent material is excited by such a hot spot, a higher resolution can be obtained.

FIG. 2 illustrates the fluorescent materials in an optical imaging system according to the related art when a light source is applied.

Referring to FIG. 2, the fluorescent materials are shown as dots. As a light source is applied, the fluorescent materials within a particular area may enter an excited state.

However, the area in which the fluorescent materials are excited cannot be reduced below a particular size, even when dimer nanopillars are used. Thus, there is a limit to the level or resolution that can be provided by a conventional TIR optical imaging system.

SUMMARY

An aspect of the invention provides an optical imaging system that offers a resolution higher than the diffraction limit.

To achieve the objective above, an aspect of the invention provides an optical imaging system that includes: a substrate on which a specimen dyed with a fluorescent material is placed; a multiple number of dimer nanopillars formed on the substrate; and a light source unit configured to provide a light source to the substrate, where the light source unit provides an incident ray to the substrate from a first light source to excite the fluorescent material, and afterwards turns off the first light source and activates a second light source and a third light source simultaneously to provide incident rays to the substrate.

The first light source may provide an incident ray having a first wavelength that is configured to excite the fluorescent material and cause the fluorescent material to emit light.

The second light source and the third light source may provide incident rays having a second wavelength that is configured to turn off the light emission of the fluorescent material.

It may be desirable to configure the incident rays provided by the second light source and the third light source such that the difference in incident angles is 90 degrees.

It may be desirable for the incident ray provided by the second light source and the incident ray provided by the third light source to have a phase difference of a half wavelength.

The second light source and the third light source may provide rays having phases and incident angles that are configured to form hotspots on both sides adjacent to an electric field hotspot generated by the first light source.

The second light source and the third light source may provide the incident rays within a time during which the fluorescent material is excited and light emission is maintained after the first light source is turned off.

The area in which the fluorescent material is excited by the hotspot formed by the first light source may partially overlap the area in which the fluorescent material is excited by the hotspots formed by the second light source and the third light source.

Another aspect of the invention provides an optical imaging system that includes: a substrate on which a specimen dyed with a fluorescent material is placed; a multiple number of dimer nanopillars formed on the substrate; and a light source unit configured to provide a light source to the substrate, where the light source unit provides a first incident ray for forming a first hotspot in a gap between the dimer nanopillars, and afterwards turns off the first incident ray and provides a second incident ray for forming two hotspots on both sides adjacent to the first hotspot.

The second incident ray may be a combination of independent rays provided by two light sources.

The first incident ray may have a frequency that is configured to be capable of exciting the fluorescent material and causing the fluorescent material to emit light.

The second incident ray may have a frequency that is configured to be capable of turning off the light emission of the fluorescent material.

The two light sources for providing the second incident ray may provide rays independently to the substrate with an angle difference of 90 degrees.

The light sources for providing the second incident ray may provide rays independently to the substrate with a phase difference of a half wavelength.

The second incident ray may be provided within a time during which the fluorescent material excited by the first incident ray maintains light emission after the first light source is turned off.

An optical imaging system according to an embodiment of the invention can provide a resolution that is higher than the diffraction limit.

Additional aspects and advantages of the present invention will be set forth in part in the description which follows, and in part will be obvious from the description, or may be learned by practice of the invention.

DETAILED DESCRIPTION

Figure 1:
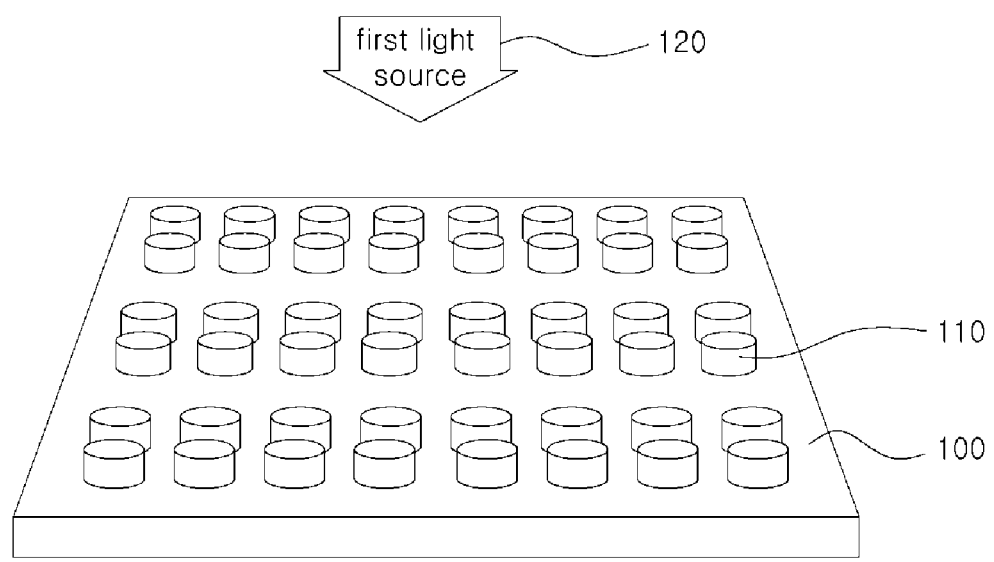
FIG. 1 illustrates the structure of light incidence in an optical imaging system according to the related art.
Figure 2:
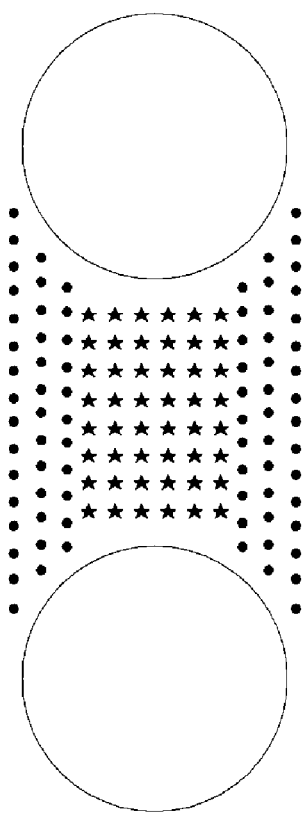
FIG. 2 illustrates fluorescent materials in an optical imaging system according to the related art when a light source is applied.

As the present invention allows for various changes and numerous embodiments, particular embodiments will be illustrated in the drawings and described in detail in the written description. However, this is not intended to limit the present invention to particular modes of practice, and it is to be appreciated that all changes, equivalents, and substitutes that do not depart from the spirit and technical scope of the present invention are encompassed in the present invention. In describing the drawings, like reference numerals are used for like elements.

Certain embodiments of the invention are described below in more detail with reference to the accompanying drawings.

Figure 3:
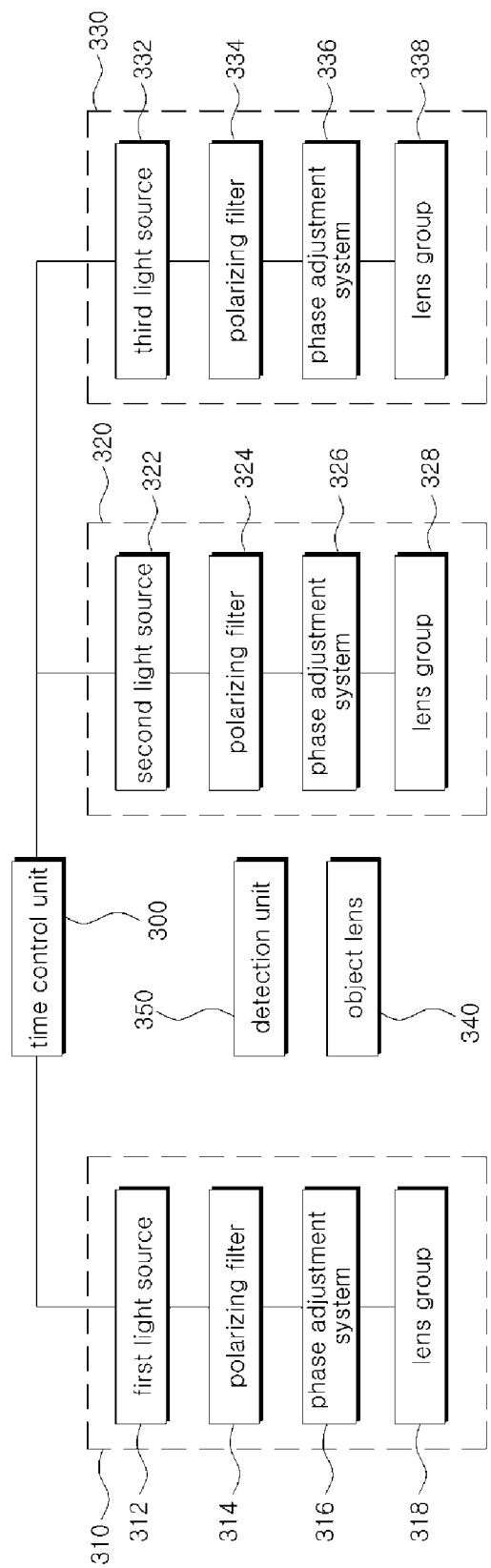
FIG. 3 is a block diagram illustrating the modular composition of an optical imaging system according to an embodiment of the invention.

FIG. 3 is a block diagram illustrating the modular composition of an optical imaging system according to an embodiment of the invention.

Referring to FIG. 3, an optical imaging system according to an embodiment of the invention can include a time control unit 300, a first light source unit 310, a second light source unit 320, a third light source unit 330, an objective lens 340, and a detection unit 350.

The first light source unit 310, second light source unit 320, and third light source unit 330 may serve to provide incident rays onto the substrate on which a specimen may be placed. The first light source unit 310, second light source unit 320, and third light source unit 330 may provide the incident rays from preconfigured angles, and the turning on/off of each light source unit 310, 320, 330 may be controlled by the time control unit 300.

According to an embodiment of the invention, multiple light sources may be turned on or off with a time discrepancy to minimize the area in which the fluorescent material is excited and thereby improve resolution, and the time control unit 300 may perform the on/off control of the light sources for improving resolution. The specific method by which the time control unit controls the multiple light sources will be described later in more detail with reference to other drawings.

FIG. 3 illustrates an example in which three light source units 310, 320, 330 are provided, but the physical number of light source units 310, 320, 330 can be two. In the present specification, the light source units are merely differentiated according to the properties of the incident rays provided and do not necessarily represent physically independent light source units. As described later in more detail, the first light source unit 310, second light source unit 320, and third light source unit 330 are referred to as different light source units merely because they provide incident rays of which at least one of the phase, frequency, and incident direction is different, and the first light source unit 310, second light source unit 320, and third light source unit 330 do not need to by physically different light sources.

Each light source unit 310, 320, 330 may include a light source 312, 322, 332, a polarizing filter 314, 324, 334, a phase adjustment system 316, 326, 336, and a lens group 318, 328, 338.

The light source 312, 322, 332 may be a lighting device for applying light. The light provided by the light source 312, 322, 332 may generate plasmon resonance in the area of nano-structured dimer pillars described later on.

According to an embodiment of the invention, a light source 312, 322, 332 may provide an incident ray that is capable of turning on (spontaneous emission) or turning off (induced emission) the fluorescent material with which a specimen is dyed.

The polarizing filter 314, 324, 334 may serve to only pass rays of a particular mode. For example, the light provided by the light source 312, 322, 332 may be one of two modes, a TEM (Transverse Electro Magnetic) mode and a TM (Transverse Magnetic) mode, and the polarizing filter 314, 324, 334 may pass only rays belonging to the TM mode.

Although it is not illustrated in FIG. 3, the light provided by a light source 312, 322, 332 can also pass through a beam expander before passing through the polarizing filter 314, 324, 334.

The phase adjustment system 316, 326, 336 may serve to adjust the phase of the light that has passed through the polarizing filter 314, 324, 334. The phase adjustment system 316, 326, 336 can adjust the phase of the light by delaying the phase of the light source.

As will be described later on, the phase properties of rays provided by the first light source unit 310 are not critically important in implementing an embodiment of the invention, and as such, the phase adjustment system 316 in the first light source unit 310 can be omitted. Of course, the first light source unit 310 can include a phase adjustment system 316 to provide other effects.

The lens group 318, 328, 338 may serve to control the direction and incident area of the incident ray applied by a light source. A lens group 318, 328, 338 may configure the direction and properties in such a way that an incident angle necessary for the operation of an embodiment of the invention is obtained.

Figure 4:
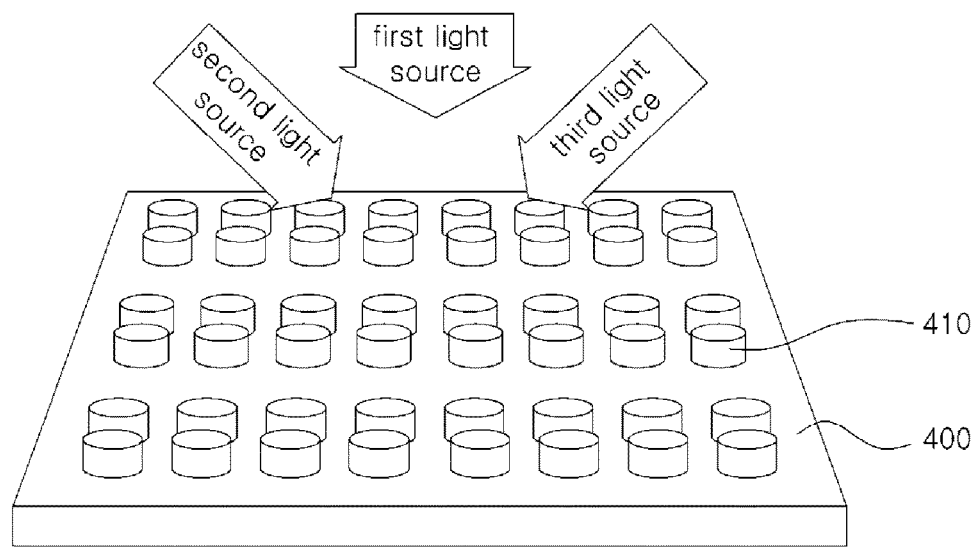
FIG. 4 illustrates the structure of light incidence in an optical imaging system according to an embodiment of the invention.

FIG. 4 illustrates the structure of light incidence in an optical imaging system according to an embodiment of the invention.

Referring to FIG. 4, an optical imaging system according to an embodiment of the invention may include a substrate 400 and multiple dimer nanopillars 410 formed on the substrate, and a specimen dyed with a fluorescent material may be placed on the substrate 400.

The dimer nanopillars may be formed such that two nanopillars are adjacent to each other, with a narrow gap present between the two nanopillars. The dimer nanopillars can be arranged regularly in constant intervals or can be arranged sporadically without following a particular rule.

While FIG. 4 illustrates dimer nanopillars 410 that have a circular cross section, the cross sections of the dimer nanopillars can be implemented in other forms such as triangular, rectangular shapes, etc.

The dimer nanopillars 410 can be made from at least one of silver (Ag), gold (Au), platinum (Pt), and aluminum (Al), where certain nanopillars can be made from different metals.

As described above, the turning on/off of the light sources may be controlled by the time control unit 300. Preliminarily, the first light source unit 310 may be activated, and the second light source unit 320 and third light source unit 330 may be deactivated.

A first incident ray provided by the first light source unit 310 may be provided with a wavelength that is capable of causing the fluorescent material to emit light (spontaneous emission). When the first incident ray is applied, the surface plasmons present in the gaps between the dimer nanopillars 410 may combine with the incident ray to generate a strong electric field. The area in which a strong electric field is generated thus is referred to as a hotspot, and the phenomenon relating to the occurrence of hotspots is referred to as plasmon resonance.

When a hotspot is generated in a localized area by the plasmon resonance phenomenon, the fluorescent material with which the specimen is dyed may emit fluorescent signals, and the area in which the fluorescent signals are excited is proportional to the size of the hotspot (although the two areas are not exactly the same).

As described above, the area of a hotspot and the area in which the fluorescent material is excited cannot be reduced below a particular size, imposing a limit to the resolution of the optical imaging system.

When the fluorescent material dyed into the specimen is excited by the first light source and emits light, the time control unit 300 may deactivate the first light source unit 310 and activate the second light source unit 320 and third light source unit 330 to apply a second incident ray from the second light source and third light source.

Here, it can be desirable for the area of incidence of the first light source to be the same as the area of incidence of the second light source and third light source, but the invention is not limited thus.

As long as the first light source can provide light to a preset area, the incidence angle and the phase of the light may not be important. However, optimal performance can be provided when the incidence angle is 0 degrees or +45 degrees.

However, it may be desirable for the second light source and the third light source to provide light at different angles, preferably with the second light source applying light at an angle of +45 degrees and the third light source applying light at an angle of −45 degrees with respect to the substrate. That is, the second light source and the third light source may provide light to the same area but with an angle difference of 90 degrees between the light applied respectively. The angle difference between the second light source and the third light source is not determined definitively and can be adjusted according to the usage environment.

According to an embodiment of the invention, the second light source and the third light source may apply rays with a frequency that can turn off the excited fluorescent material (induced emission). The frequency capable of causing induced emission may be determined beforehand according to the type of fluorescent material, and the second light source and third light source may apply the rays with the corresponding frequencies.

The combined light of the second light source and third light source can also generate a hotspot in which the intensity of an electric field is magnified in a particular area, and the electric field of the area in which a hotspot is generated may turn off the fluorescent material that is emitting light (induced emission).

In order to cause induced emission in the fluorescent material that is emitting light, the second light source and the third light source may provide the substrate with rays that have a phase difference of a half wavelength. Unlike the case in which only a coherent ray is incident at the dimer nanopillars 410, the incidence of two rays having different phases may cause interference to the electric near-field excited in the dimmers, so that a change may occur in the electric near-field pattern according to the phase difference, even if the two light sources have the same frequency. Compared with the near field generated by a single light source, the two light sources with a phase difference of a half wavelength may form a field in which the intensity is the lowest in a portion of the hotspot area of the single light source, making it possible to improve resolution as intended by the present invention.

Figure 5:
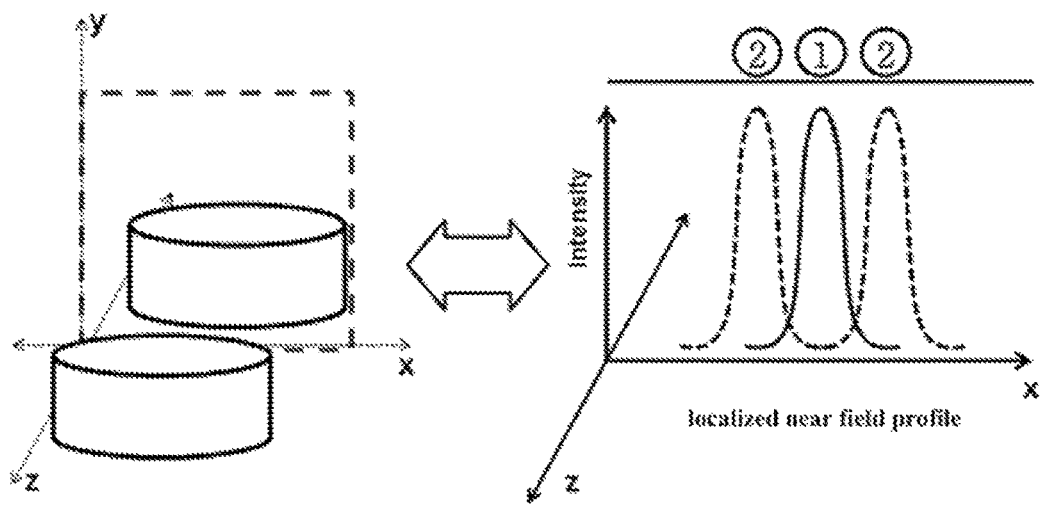
FIG. 5 illustrates the electric field generated by a first light source and the electric fields generated by a second and a third light source.

FIG. 5 illustrates the electric field generated by a first light source and the electric fields generated by a second and a third light source.

In FIG. 5, the x axis represents the spatial coordinates of a gap between dimer nanopillars, and the y axis represents the intensity of the electric field. The first electric field, indicated as a solid line, is the electric field generated by the first light source, and the second electric field, indicated as dotted lines, is the electric field generated by the second light source and third light source.

Referring to FIG. 5, the electric field generated by the first light source may have a peak value at a particular area between the dimer nanopillars. As described above, an area where the peak value is formed is a hotspot.

However, the second electric field generated by the second light source and third light source may have the lowest value in the hotspot area of the first electric field generated by the first light source, and the hotspots of the second electric field may be formed on both sides near the hotspot of the first electric field.

The reason why the intensity is the lowest in the hotspot area of the first electric field and the hotspots are formed on both sides of the hotspot of the first electric field is because the phase difference between the second light source and third light source is set to be about a half wavelength.

Figure 6:
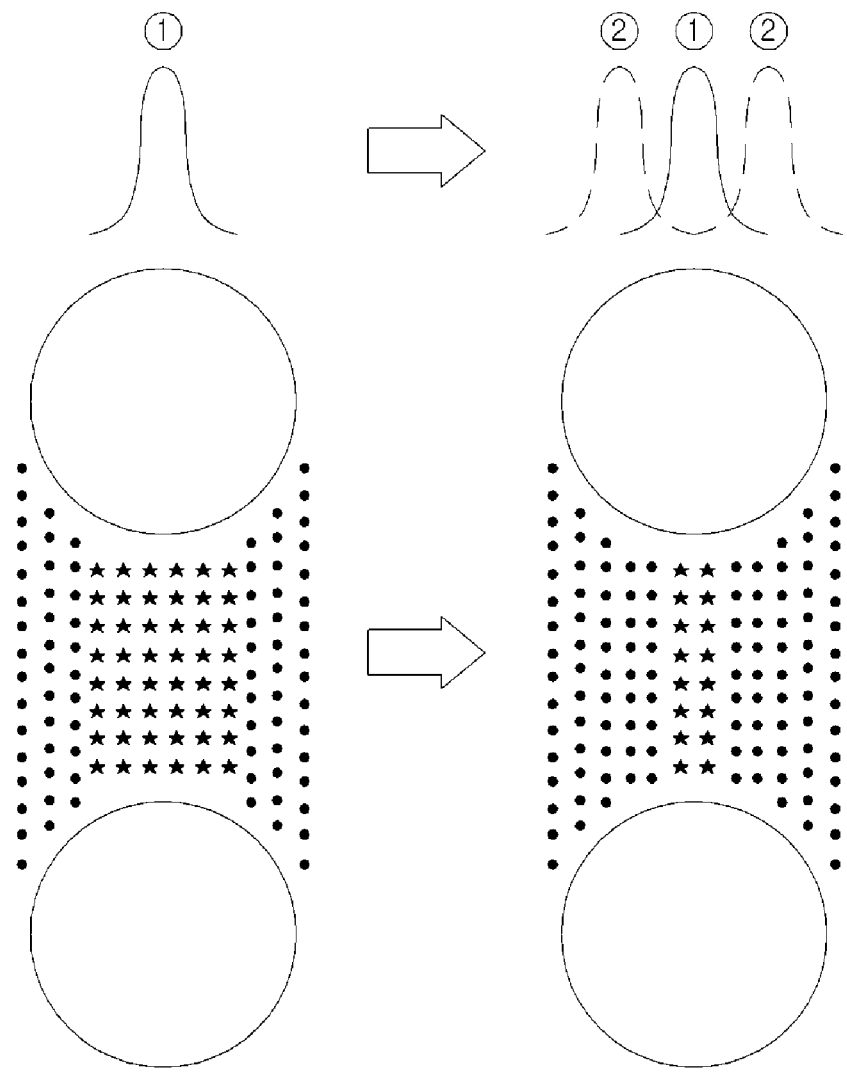
FIG. 6 illustrates the illumination area of fluorescent materials excited by a first light source and the illumination area changed by a second light source and a third light source.

FIG. 6 illustrates the illumination area of fluorescent materials excited by a first light source and the illumination area changed by a second light source and a third light source.

Referring to FIG. 6, it can be seen that, when only the first light source is provided to the substrate having dimer nanopillars, the fluorescent material in a particular area is made to radiate light due to the hotspot generated by the first light source.

As the time control unit deactivates the first light source unit and activates the second light source unit and third light source unit to apply incident rays by way of the second light source and third light source, the hotspots of the second electric field may be formed on both sides of the hotspot of the first electric field caused by the first light source, where the second electric field turns off the fluorescent material that is emitting light in the hotspot area (induced emission).

Thus, as the second electric field is generated by the second light source and third light source, the state of light emission is turned off at the sides of the fluorescent area where light was being emitted due to the first light source, and as a result, the excited fluorescent area may be reduced, as illustrated in FIG. 6.

As described above, there is a limit to the size of the hotspots and the size of the fluorescent area that can be excited by a hotspot, which imposed a limit on the resolution of an optical imaging system based on total reflection.

However, by using a technique of providing light sources alternatingly with a time discrepancy according to an embodiment of the invention, the fluorescent area that is excited can be reduced without being limited by the diffraction limit, making it possible to provide improved resolution.

Figure 7:
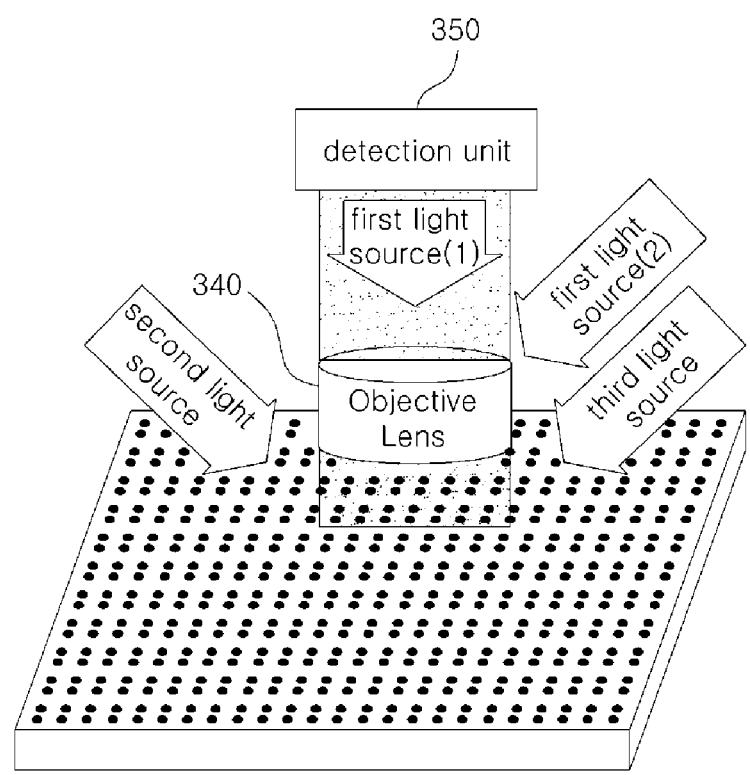
FIG. 7 illustrates the detection operation of an optical imaging system according to an embodiment of the invention.

FIG. 7 illustrates the detection operation of an optical imaging system according to an embodiment of the invention.

When the fluorescent material emits light in an area smaller than the diffraction limit, by virtue of providing the first light source and the second light source and third light source with a time discrepancy, the objective lens 340 may serve to magnify an area of interest. Here, an area of interest can include at least one of the areas in which the fluorescent material emits light.

The detection unit 350 may serve to obtain an image for portions magnified by the objective lens 340. The detection unit 350 may include a camera, such as, for example, a CCD camera.

FIG. 7 illustrates two first light sources, but this is to indicate that the incident angle of the first light source can be 0 degrees or +45 degrees, and is not intended to mean that there are actually two first light sources provided.

Of course, the first light source can be provided in an angle other than 0 degrees or +45 degrees.

Figure 8:
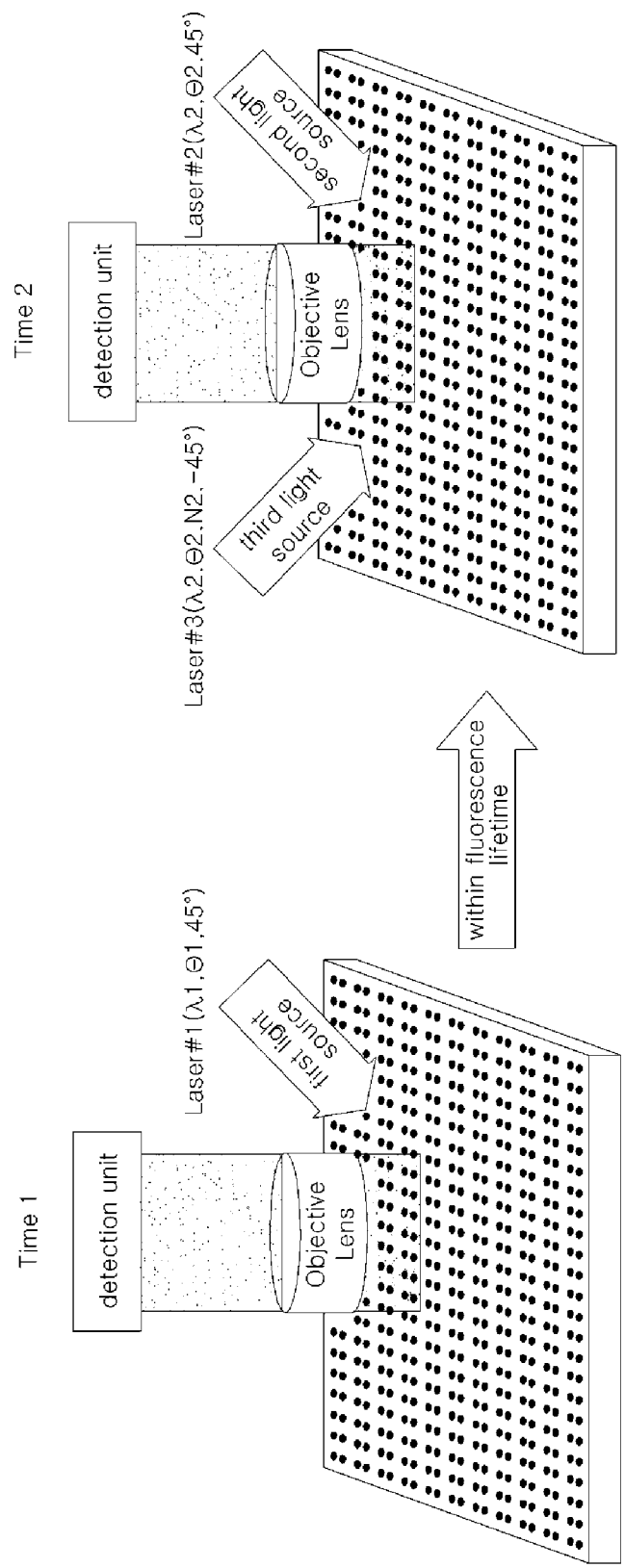
FIG. 8 illustrates an operation of controlling the light sources according to an embodiment of the invention.

FIG. 8 illustrates an operation of controlling the light sources according to an embodiment of the invention.

Referring to FIG. 8, the time control unit may first activate only the first light source unit 310 and deactivate the second light source unit 320 and third light source unit 330, so that only the incident ray from the first light source is applied to the substrate.

The first light source may have a wavelength $2d$ that enables light emission in the fluorescent material. When the first light source is applied, an electric field hotspot may be generated at a particular point in a gap between the dimer nanopillars, and the hotspot thus generated may cause the fluorescent material in a particular area to emit light.

When the fluorescent material is made to emit light by the first light source, the time control unit 300 may turn off the first light source unit 310 and activate the second light source unit 320 and the third light source unit 330.

According to an embodiment of the invention, the time at which the second light source unit 320 and third light source unit 330 are activated, after the first light source unit 310 is turned off, should be within the time during which the light emission by the fluorescent material excited by the first light source of the first light source unit 310 is maintained (i.e. lifetime). The second light source unit 320 and the third light source unit 330 may be activated simultaneously.

As described above, it may be desirable to provide the second light source and the third light source at angles of −45 degrees and +45 degrees, and it may be desirable if the incidence areas of the second light source and the third light source are the same.

Also, the wavelengths of the second light source and the third light source may be the same, being a wavelength $2d$ that enables the turning off of the fluorescent material that is emitting light. The phase difference of the second light source and the third light source may be a half wavelength $(\lambda/2)$.

As the second light source and the third light source are applied while the light emission of the fluorescent material caused by the first light source is being maintained, the light emission of the fluorescent material in the areas corresponding to the hotspots of the second light source and third light source may be turned off.

The first light source unit 310 does not have to be a physically separate from either one of the second light source unit 320 and third light source unit 330. Since the wavelength, phase, direction, etc., of a light source unit can be adjusted, it is possible to have the same light source unit operate as the first light source unit and also as either one of the second light source unit and third light source unit.

While the present invention has been described above using particular examples, including specific elements, by way of limited embodiments and drawings, it is to be appreciated that these are provided merely to aid the overall understanding of the present invention, the present invention is not to be limited to the embodiments above, and various modifications and alterations can be made from the disclosures above by a person having ordinary skill in the technical field to which the present invention pertains. Therefore, the spirit of the present invention must not be limited to the embodiments described herein, and the scope of the present invention must be regarded as encompassing not only the claims set forth below, but also their equivalents and variations.

What is claimed is:

1. An optical imaging system comprising:
   a substrate having placed thereon a specimen dyed with a fluorescent material;
   a plurality of dimer nanopillars formed on the substrate; and
   a light source unit configured to provide a light source to the substrate, wherein
   the light source unit provides an incident ray to the substrate from a first light source to excite the fluorescent material, and afterwards turns off the first light source and activates a second light source and a third light source simultaneously to provide incident rays to the substrate,
   the second light source and the third light source provide incident rays having a second wavelength, the second wavelength configured to turn off an emission of light by the fluorescent material,
   a difference between incident angles of the incident rays provided by the second light source and the third light source is 90 degrees,
   the incident ray provided by the second light source and the incident ray provided by the third light source have a phase difference of a half wavelength, and the incident ray provided by the second light source is provided at an angle of +45 degrees with respect to the substrate, and the incident ray of the third light source is provided at an angle of −45 degrees with respect to the substrate.

2. The optical imaging system of claim 1, wherein the incident ray provided by the first light source has a first wavelength, the first wavelength configured to excite the fluorescent material and cause the emission of light by the fluorescent material.

3. The optical imaging system of claim 1, wherein the second light source and the third light source provide rays having phases and incident angles configured to form hotspots on both sides adjacent to an electric field hotspot generated by the first light source.

4. The optical imaging system of claim 3, wherein an area in which the fluorescent material is excited by the hotspot formed by the first light source partially overlaps an area in which the fluorescent material is excited by the hotspots formed by the second light source and the third light source.

5. The optical imaging system of claim 1, wherein the second light source and the third light source provide the incident rays within a time during which the fluorescent material is excited and light emission is maintained after the first light source is turned off.

* * * * *